(12) United States Patent
Dellenbusch

(10) Patent No.: US 6,363,931 B1
(45) Date of Patent: Apr. 2, 2002

(54) ANESTHETIC GAS OCCLUDER

(76) Inventor: Kent J. Dellenbusch, 208 N. 74th St., Milwaukee, WI (US) 53213

( * ) Notice: Subject to any disclaimer, the term of this patent is extended or adjusted under 35 U.S.C. 154(b) by 0 days.

(21) Appl. No.: 09/649,450

(22) Filed: Aug. 25, 2000

(51) Int. Cl.[7] .............................................. A62B 9/04
(52) U.S. Cl. ............. 128/202.27; 128/910; 128/207.14
(58) Field of Search ........................... 128/802.27, 912, 128/205.12, 207.14, 207.15; 600/499; 258/18; 248/228.7, 231.81

(56) References Cited

U.S. PATENT DOCUMENTS

| | | | |
|---|---|---|---|
| 4,633,890 A | | 1/1987 | Carden |
| 5,057,093 A | * | 10/1991 | Clegg et al. ................ 604/283 |
| 5,385,324 A | * | 1/1995 | Pryor et al. .............. 248/231.7 |
| 5,695,162 A | * | 12/1997 | DiCastro ................ 248/231.81 |
| 5,772,166 A | * | 6/1998 | Adams .................... 248/231.8 |
| 5,937,851 A | * | 8/1999 | Serowski et al. ...... 128/202.27 |
| 5,960,746 A | * | 10/1999 | Salts ........................... 119/756 |
| 6,026,810 A | * | 2/2000 | Baird .................... 128/207.14 |

* cited by examiner

*Primary Examiner*—John G. Weiss
*Assistant Examiner*—V. Srivastava
(74) *Attorney, Agent, or Firm*—Ryan Kromholz & Manion, S.C.

(57) ABSTRACT

An occluder for supporting and preventing escape of anesthesia gases through face masks when not in use includes a C-shaped support base. The base consists of a flat base plate adapted to fit beneath a surgical mattress, a side plate located in a plane normal to that of the base plate which has a height equal to the thickness of a standard surgical mattress, and a top plate which is in a plane parallel to that of the base plate. A solid cylindrical support shaft is integral with and extends upwardly from the top plate. Preferably the cylindrical support shaft has a main body portion approximately 15 mm in diameter and a top portion of reduced diameter which is preferably 13 mm in diameter. The components of the occluder are preferably formed of a non-ferrous metal such as aluminum.

7 Claims, 3 Drawing Sheets

ANESTHETIC GAS OCCLUDER

The invention relates to a device for occluding anesthetic gases used in the practice of surgery dentistry and anesthesiology. More particularly, the invention relates to a device for supporting an anesthetic mask and connected gas circuit conduits and fittings while occuluding the gas discharge opening to shut off the gas flow during periods of time when the mask is not in use.

BACKGROUND OF THE INVENTION

Anesthetic gases are used in many patient care facilities such as operating rooms, radiology, MRI installations or dental offices. The long term exposure to such gases, which, after their escape, are a form of atmospheric pollutant, are suspected to have serious adverse health effects on health care workers who are repeatedly exposed thereto.

Various suggestions have been made for alleviation of this problem. For example, in U.S. Pat. No. 4,633,890 it was suggested that an exhaust tube be provided for the purpose of venting such gases out of the immediate area. However, such devices have not successfully eliminated the problem. This is because a significant amount of the anesthetic gases escape through the exhaust system and must still be dealt with as they eventually escape into the atmosphere. Thus, a need has continued to exist for improved devices and methods for safeguarding healthcare workers against exposure to such escaping anesthetic gases.

SUMMARY OF THE INVENTION

It is an important object of the present invention is to provide an improved device for occluding anesthesia circuits. An important aspect of the invention is the provision of an occluding device which can close the opening of a standard sized face mask and as well as that of a relatively smaller pediatric mask.

Another significant advantage of the invention relates to the provision of an occluder which conveniently supports the mask when not in use while at the same time occluding the gas inlet and thus preventing escape of anesthetic gases through the mask when not in use. Yet another aspect of the invention is the provision on the occluder of a rectangular "U" shaped bracket which is adapted to fit over the side of an operating table mattress pad.

Still further aspects of the invention relate to the provision of a support/occluder device which is non-ferrous and thus is compatible with MRI. The non-ferrous material also does not hold an ionic charge for as long a period of time as do ferrous metals when used near x-rays. A still further aspect of the invention relates to the economy of manufacture of the device compared to prior art devices, as well the ease of use.

In accordance with a modified embodiment of the invention, the occluder is provided with a telescoping support stem. This embodiment, thus, provides an adjustable version of the invention.

Briefly, the invention provides an improved occluder for supporting and preventing escape of anesthesia gases through face masks when not in use which includes a C-shaped support base. The base consists of a flat base plate adapted to fit beneath a surgical mattress, a side plate located in a plane normal to that of the base plate which has a height equal to the thickness of a standard surgical mattress, and a top plate which is in a plane parallel to that of the base plate. A solid cylindrical support shaft is integral with and extends upwardly from the top plate. Preferably the cylindrical support shaft has a main body portion approximately 15 mm in diameter and a top portion of reduced diameter which is preferably 13 mm in diameter. The components of the occluder are preferably formed of a non-ferrous metal such as aluminum.

Further objects and advantages of the invention will be apparent from the attached claims, the following detailed description and the accompanying drawings.

DETAILED DESCRIPTION OF THE INVENTION

Figure 2:
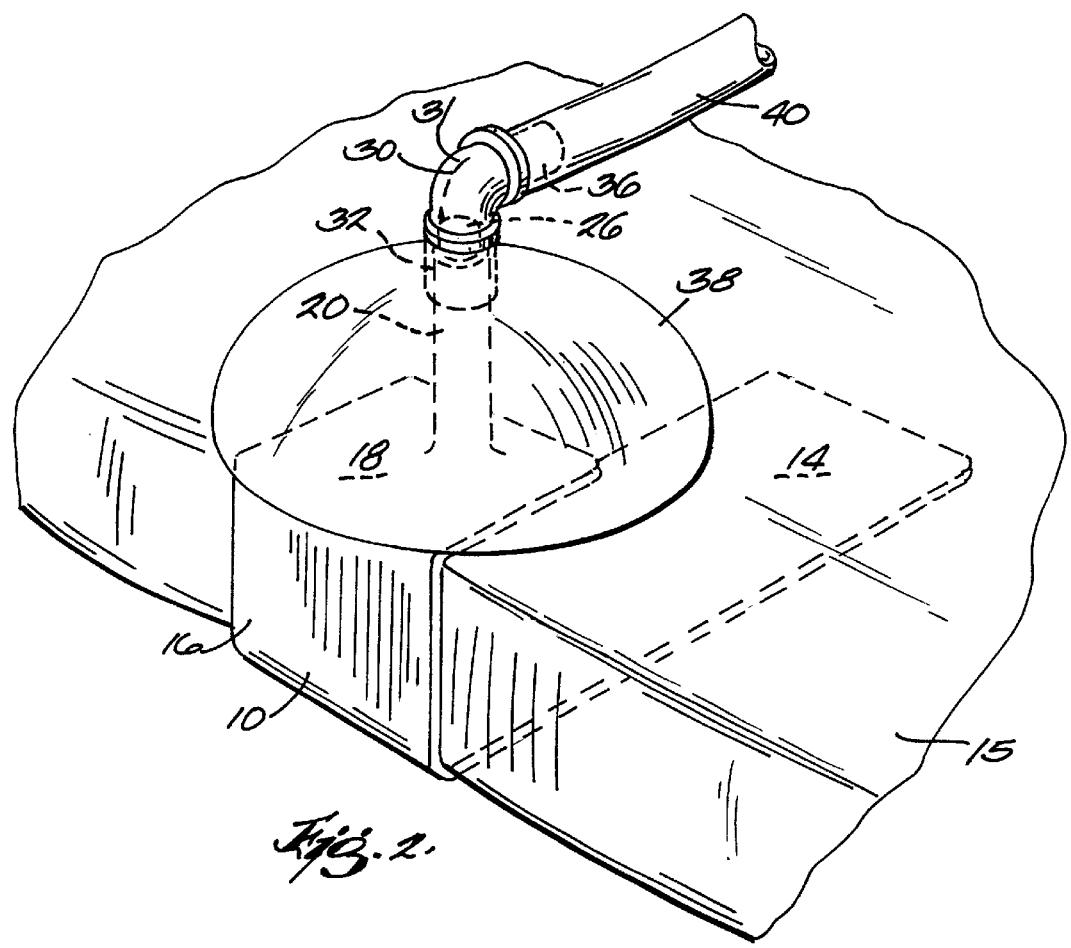
FIG. 2 is a fragmentary perspective view illustrating the occluder of FIG. 1 in conjunction with a surgical mask attached to an anesthetic gas conduit and an operating room mattress both shown in fragmentary fashion with some hidden parts shown by phantom lines.
Figure 1:
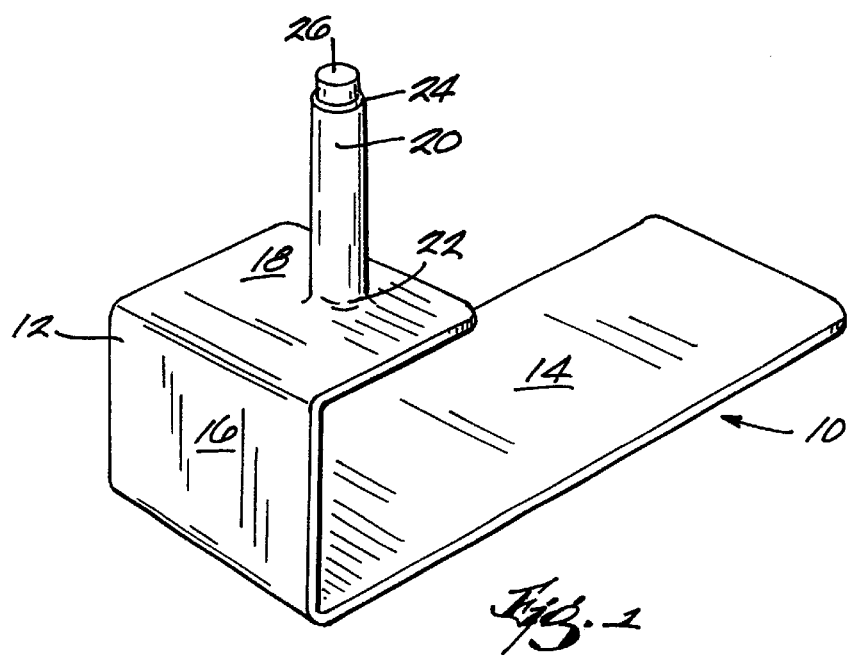
FIG. 1 is a perspective view of an occluder device in accordance with the invention.

Referring more particularly to the drawings, an occluder device of this invention is illustrated generally by numeral 10. As best seen in FIGS. 1 and 2, occluder 10 includes a C-shaped body 12 which enables the occluder to be firmly supported on a standard operating room mattress 15. The C-shaped support base 12 includes a bottom panel 14 which is of a width and length sufficient to anchor the occluder 10 firmly under the mattress 15 so as to stabilize the occluder 10 on the mattress 15. Preferably, the length is in the range of six to eight inches and the width is at least four inches.

End panel 16 is of a height equal to a thickness of a standard mattress 15, i.e., 2⅞ inches. Upper plate 18 supports an occluder shaft 20. Preferably the shaft 20 is attached to the plate 18 by means of a weldment 22. However, it will be apparent to those skilled in the art that shaft 20 could also be attached by mechanical means such as a counter-sunk screw extending upwardly through plate 18 into a threaded socket formed in the bottom of shaft 20. However, a weldment 22 as illustrated is greatly preferred because of the avoidance thereby of any crevices which could harbor harmful microbes. It will also be readily apparent from FIG. 1 that the occluder 10 can be easily removed from the mattress 15 and successfully sanitized since it is of a seamless construction.

The upper end of occluder shaft 20 is preferably provided with a shoulder 24 above which an end section 26 of slightly reduced diameter extends. As will subsequently be shown in greater detail, the end section 26 is used in conjunction with pediatric masks which are of smaller dimensions than a standard adult mask.

Figure 3:
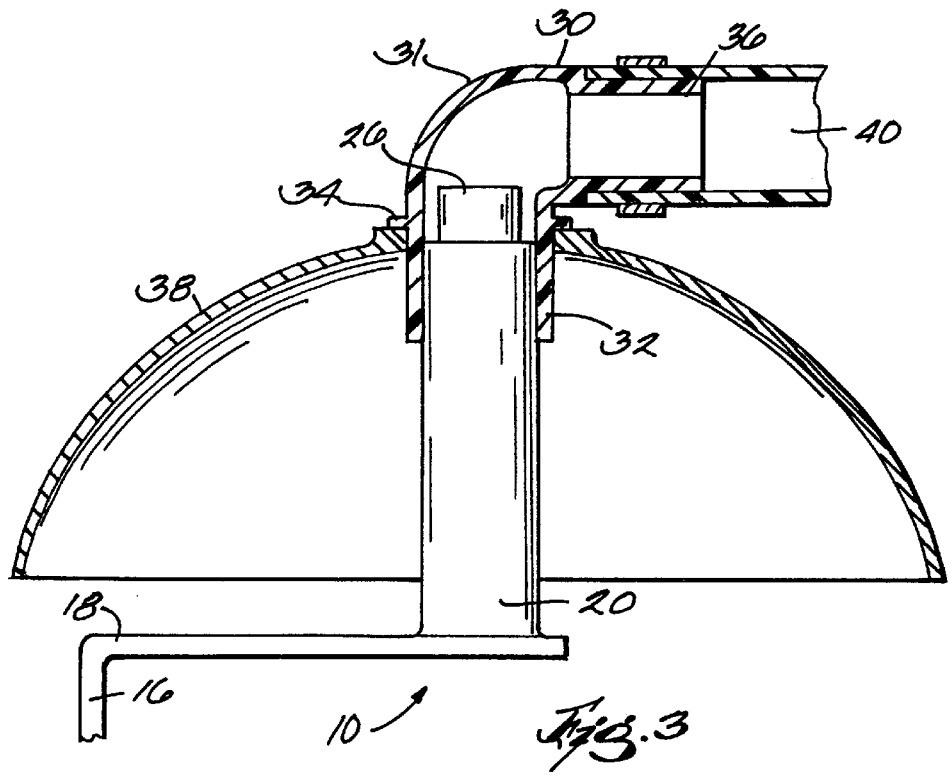
FIG. 3 is a cross-sectional fragmentary view showing the occluder and face mask of FIG. 2.

Referring to FIG. 3 there is also shown an elbow connector 30 of a type generally attached to a face mask 38 for the purpose of discharging anesthetic gas into the mask from a supply conduit 40. Elbow 30 includes a body portion 31 bent at right angles with a mask engaging end 32 and a exterior shoulder 34 which assists in properly locating the elbow end 32 in the opening of the mask 38. The opposite end 36 of elbow 30 is of a reduced diameter adapted to fit tightly into the inside diameter of tubing 40 which is connected to a supply (not shown) of anesthetic gases.

In order to fit tightly in the elbow 30 and thereby close the anesthetic gas circuit against discharge of gases when the circuit is not in use, the shaft 20 should have a diameter of 15 mm. In order to also accommodate and successfully occlude pediatric masks such as mask 48 shown in FIG. 4, as well, the end section 26 of reduced diameter should have a diameter of 13 mm.

Figure 4:
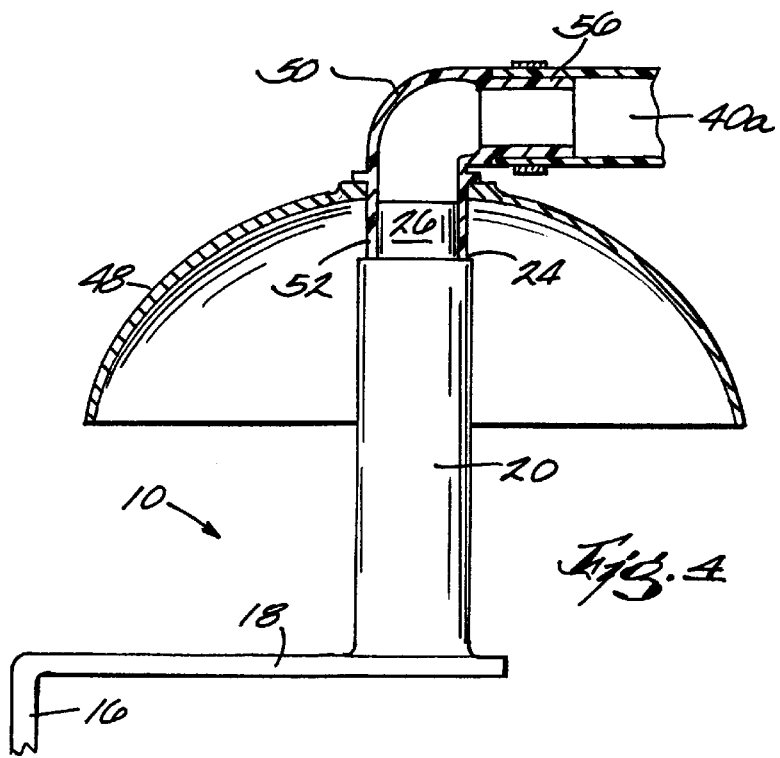
FIG. 4 is a sectional view similar to FIG. 3 but showing the occluder in use in conjunction with a pediatric mask.

As also seen in FIG. 4, a pediatric mask 48 is provided with an elbow connector 50 having an end 52 adapted to fit tightly around the end section 26 of the occluder 10. Connector 50 has an opposite end 56 adapted to tightly connect to the interior of gas supply conduit 40*a*.

Figure 5:
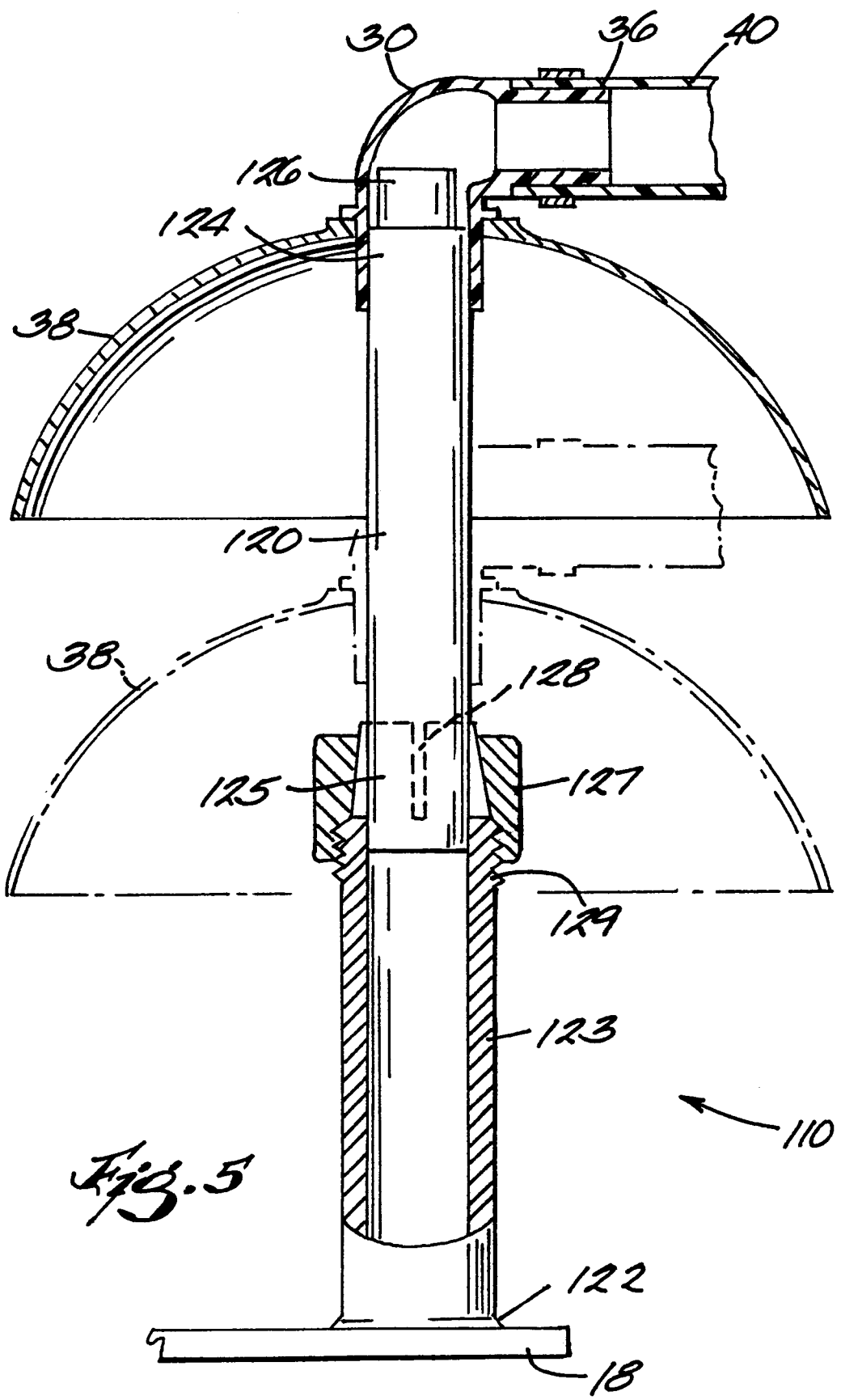
FIG. 5 is a cross-sectional view of a modified embodiment of the invention showing an alternative position thereof by means of phantom lines.

Referring to FIG. 5, yet another embodiment of the invention is illustrated. In this embodiment a height adjustable occluder 110 is provided. In connection with this embodiment numerals identical to those assigned to components of the earlier described embodiments relate to the same components and thus are not discussed again in detail in connection with the embodiment of FIG. 5.

In order to provide adjustability, a hollow tubular stem 123 is affixed by means of a weldment 122 to plate 18. The upper end 125 of hollow stem 123 is provided with slots 128 which allow flexing of the end 125 around the exterior of a solid upper stem 120. A nut 127 having a tapered interior structure, as illustrated, is utilized in known fashion to compress the end 125 around the stem 120 when nut 127 is advanced on threads 129. The height of the upper end 124, 126 of the occluder 110 is, thus, made adjustable. This embodiment thus enhances the convenience of using the occluder in varying environments. As in the case of the earlier embodiment the shoulder 124 of stem 120 is adapted to close the end of connector 30 thus preventing gas from conduit 40 from entering the room in which the mask 38 is being deployed. Also, as in the case of the earlier embodiment, an end section 126 of reduced diameter is provided for use in connection with pediatric masks.

It will be understood by those skilled in the art that the invention is not limited to the precise forgoing preferred embodiments and thus variations may be made thereto. The scope of the invention is thus determined by interpretation of the accompanying claims.

What is claimed is:

1. An occluder for supporting and preventing escape of anesthesia gases through face masks when not in use comprising:

a C-shaped support base with a flat base plate adapted to fit beneath a surgical mattress, a side plate located in a plane normal to that of said base plate having a bottom edge contiguous with said base plate and having a height equal to the thickness of a standard surgical mattress, and a top plate contiguous with an upper edge of said side plate, said top plate being in a plane parallel to that of said base plate; and, a solid cylindrical support shaft supported on and extending upwardly from said top plate, said cylindrical support shaft having a main body portion approximately 15 mm in diameter.

2. An occluder according to claim 1 wherein said support shaft comprises a cylindrical solid top portion of reduced diameter.

3. An occluder according to claim 1 wherein said support shaft extends upwardly at right angles to said top plate.

4. An occluder according to claim 2 wherein said support shaft is welded to said top plate.

5. An occluder according to claim 1 wherein said C-shaped support base and said cylindrical support shaft are formed of aluminum.

6. An adjustable occluder for supporting and preventing escape of anesthesia gases through face masks when not in use comprising:

a C-shaped support base with a flat base plate adapted to fit beneath a surgical mattress, a side plate located in a plane normal to that of said base plate having a bottom edge contiguous with said base plate and having a height equal to the thickness of a standard surgical mattress, and a top plate contiguous with an upper edge of said side plate, said top plate being in a plane parallel to that of said base plate;

a hollow cylindrical support shaft supported on and extending upwardly from said top plate, said hollow support shaft having an upper end for adjustably receiving an occluder stem having a main body portion approximately 15 mm in diameter, and, means on said upper end for fixing said stem at selected heights within said hollow support shaft.

7. An occluder according to claim 6 wherein said upper end is threaded and provided with flutes, and a nut is threaded thereon, said nut having and interior taper circumscribing said fluted end whereby the stem is releasably fixed at adjustable height within said hollow shaft.

\* \* \* \* \*